(12) United States Patent
Levine et al.

(10) Patent No.: US 8,788,034 B2
(45) Date of Patent: Jul. 22, 2014

(54) SINGLE-PULSE ACTIVATION OF THE CHOLINERGIC ANTI-INFLAMMATORY PATHWAY TO TREAT CHRONIC INFLAMMATION

(75) Inventors: Jacob A. Levine, Queens, NY (US); Michael A. Faltys, Valencia, CA (US)

(73) Assignee: SetPoint Medical Corporation, Valencia, CA (US)

( * ) Notice: Subject to any disclaimer, the term of this patent is extended or adjusted under 35 U.S.C. 154(b) by 0 days.

(21) Appl. No.: 13/467,928

(22) Filed: May 9, 2012

(65) Prior Publication Data
US 2012/0290035 A1 Nov. 15, 2012

Related U.S. Application Data

(60) Provisional application No. 61/484,112, filed on May 9, 2011.

(51) Int. Cl.
*A61N 1/00* (2006.01)

(52) U.S. Cl.
USPC .......................................................... 607/2

(58) Field of Classification Search
USPC ................................................. 607/2, 72–76
See application file for complete search history.

(56) References Cited

U.S. PATENT DOCUMENTS

| | | |
|---|---|---|
| 2,164,121 A | 6/1939 | Pescador |
| 3,363,623 A | 1/1968 | Atwell |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |

(Continued)

FOREIGN PATENT DOCUMENTS

| | | |
|---|---|---|
| CN | 201230913 | 5/2009 |
| DE | 2628045 A1 | 1/1977 |

(Continued)

OTHER PUBLICATIONS

US 6,184,239, 2/2001, Puskas (withdrawn).

(Continued)

*Primary Examiner* — Scott Getzow
(74) *Attorney, Agent, or Firm* — Shay Glenn LLP

(57) ABSTRACT

Described herein are methods and systems for applying extremely low duty-cycle stimulation sufficient to treat chronic inflammation. In particular, described herein are single supra-threshold pulses of electrical stimulation sufficient to result in a long-lasting (e.g., >4 hours, greater than 12 hours, greater than 24 hours, greater than 48 hours) inhibition of pro-inflammatory cytokines and/or effects of chronic inflammation. These methods and devices are particularly of interest in treatment of inflammatory bowel disease (IBD).

20 Claims, 6 Drawing Sheets

(56) References Cited

U.S. PATENT DOCUMENTS

| | | |
|---|---|---|
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thomspon et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |

(56) References Cited

U.S. PATENT DOCUMENTS

| | | |
|---|---|---|
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 E | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,195,287 B2 | 6/2012 | Dacey, Jr. et al. |
| 8,214,056 B2 | 7/2012 | Hoffer et al. |
| 2001/0002441 A1 | 5/2001 | Boveja |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0059383 A1 | 3/2004 | Puskas |
| 2004/0111139 A1 | 6/2004 | McCreery |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0125044 A1 | 6/2005 | Tracey |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |

(56) References Cited

U.S. PATENT DOCUMENTS

| | | |
|---|---|---|
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0282906 A1 | 12/2005 | Tracey et al. |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0142802 A1 | 6/2006 | Armstrong |
| 2006/0142822 A1 | 6/2006 | Tulgar |
| 2006/0149337 A1 | 7/2006 | John |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0118177 A1 | 5/2007 | Libbus et al. |
| 2007/0118178 A1 | 5/2007 | Fukui |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0239243 A1 | 10/2007 | Moffitt et al. |
| 2007/0250145 A1 | 10/2007 | Kraus et al. |
| 2007/0255320 A1 | 11/2007 | Inman et al. |
| 2007/0255333 A1 | 11/2007 | Giftakis |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0208266 A1* | 8/2008 | Lesser et al. .............. 607/2 |
| 2008/0234790 A1 | 9/2008 | Bayer et al. |
| 2008/0249439 A1 | 10/2008 | Tracey et al. |
| 2008/0281365 A1 | 11/2008 | Tweden et al. |
| 2009/0012590 A1 | 1/2009 | Inman et al. |
| 2009/0048194 A1 | 2/2009 | Aerssens et al. |
| 2009/0062874 A1 | 3/2009 | Tracey et al. |
| 2009/0082832 A1 | 3/2009 | Carbunaru et al. |
| 2009/0105782 A1 | 4/2009 | Mickle et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |

(56) References Cited

U.S. PATENT DOCUMENTS

| | | | |
|---|---|---|---|
| 2009/0171405 | A1 | 7/2009 | Craig |
| 2009/0177112 | A1 | 7/2009 | Gharib et al. |
| 2009/0187231 | A1 | 7/2009 | Enrico et al. |
| 2009/0247934 | A1 | 10/2009 | Tracey et al. |
| 2009/0248097 | A1 | 10/2009 | Tracey et al. |
| 2009/0254143 | A1 | 10/2009 | Tweden et al. |
| 2009/0275997 | A1 | 11/2009 | Faltys et al. |
| 2009/0276019 | A1 | 11/2009 | Perez et al. |
| 2009/0281593 | A9 | 11/2009 | Errico et al. |
| 2010/0003656 | A1 | 1/2010 | Kilgard et al. |
| 2010/0010603 | A1 | 1/2010 | Ben-David et al. |
| 2010/0042186 | A1 | 2/2010 | Ben-David et al. |
| 2010/0063563 | A1 | 3/2010 | Craig |
| 2010/0125304 | A1 | 5/2010 | Faltys |
| 2010/0191304 | A1 | 7/2010 | Scott |
| 2010/0215632 | A1 | 8/2010 | Boss et al. |
| 2010/0241183 | A1 | 9/2010 | DiLorenzo |
| 2010/0249859 | A1 | 9/2010 | DiLorenzo |
| 2010/0280569 | A1 | 11/2010 | Bobillier et al. |
| 2010/0312320 | A1 | 12/2010 | Faltys et al. |
| 2011/0004266 | A1 | 1/2011 | Sharma |
| 2011/0054569 | A1 | 3/2011 | Zitnik et al. |
| 2011/0066208 | A1 | 3/2011 | Pasricha et al. |
| 2011/0092882 | A1 | 4/2011 | Firlik et al. |
| 2011/0106208 | A1 | 5/2011 | Faltys et al. |
| 2011/0190849 | A1* | 8/2011 | Faltys et al. .................. 607/50 |
| 2011/0307027 | A1 | 12/2011 | Sharma et al. |
| 2012/0065706 | A1 | 3/2012 | Vallapureddy et al. |
| 2013/0253413 | A1 | 9/2013 | Levine et al. |

FOREIGN PATENT DOCUMENTS

| | | |
|---|---|---|
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2073896 B1 | 10/2011 |
| GB | 04133 | 2/1910 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |

OTHER PUBLICATIONS

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to SHOCK, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression in shock, New York Surgical Society, New York, NY, Apr. 11, 2001.

Bernik, et al., Pharmacological stimulation of the cholinergic anti-inflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, No. 4764, pp. 652-654, Aug. 1986.

Bhattacharya, S.K. et al., Central muscarinic receptor subtypes and carrageenin-induced paw oedema in rats, Res. Esp. Med. vol. 191(1), pp. 65-76, Dec. 1991.

Bianchi et al., Suppression of proinflammatory cytokines in monocytes by a tetravalent guanylhydrazone, Journal of Experimental Medicine, vol. 183, pp. 927-936, Mar. 1996.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Blackwell, T. S. et al., Sepsis and cytokines: current status, Br. J. Anaesth., vol. 77(1), pp. 110-117, Jul. 1996.

Blum, A. et al., Role of cytokines in heart failure, Am. Heart J., vol. 135 (2), pp. 181-186, Feb. 1998.

Boldyreff, Gastric and intestinal mucus, its properties and physiological importance, Acta Medica Scandinavica (journal), vol. 89, Issue 1-2, pp. 1-14, Jan./Dec. 1936.

Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.

Borovikova et al., Efferent vagus nerve activity attenuates cytokine-mediated inflammation, Society for Neuroscience Abstracts, vol. 26, No. 102, Nov. 4-9, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

Borovikova et al., Role of the efferent vagus nerve signaling in the regulation of the innate immune response to LPS, (supplemental to SHOCK, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.

Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced shock, (Supplemental to SHOCK, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

(56) References Cited

OTHER PUBLICATIONS

Borovikova, L. V., et al., Vagus nerve stimulation attenuates the systemic inflammatory response to endotoxin, Nature, vol. 405, No. 6785: pp. 458-462, May 25, 2000.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, pp. 189-204, (month unavailable) 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cicala et al., "Linkage between inflammation and coagulation: An update on the molecular basis of the crosstalk," Life Sciences, vol. 62(20); pp. 1817-1824, Apr. 1998.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
DAS, Critical advances in spticemia and septic shock, Critical Care, vol. 4, pp. 290-296, Sep. 7, 2000.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., the interleukin-1 family: 10 years of discovery, FASEB J., vol. 8, No. 15, pp. 1314-1325, Dec. 1994.
Doshi et al., Evolving role of tissue factor and its pathway inhibitor, Crit. Care Med., vol. 30, suppl. 5, pp. S241-S250, May 2002.
Ellington et al., In vitro selection of RNA molecules that bind specific ligands, Nature, vol. 346, pp. 818-822, Aug. 30, 1990.
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(–)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, SHOCK, vol. 27, No. 4, pp. 443-447, Apr. 2007.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Guarente, Leonard, Ph. D.; Sirtuins, Aging, and Medicine; N Engl J Med; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; (month unavailable) 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby-Year Book, inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.

(56) References Cited

OTHER PUBLICATIONS

Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Neural regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (month unavailable) 2001.
Katagiri, M., et al., Increased cytokine production by gastric mucosa in patients with helicobacter pylori infection, J. Clin, Gastroenterol., vol. 25, Suppl. 1, pp. S211-S214, (month unavailable) 1997.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Krarup et al; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, SHOCK, vol. 5, No. 5, pp. 385-388, May 1996.
Kuznik, "Role of the vascular wall in the process of hemostatis," Usp Sovrem Biol., vol. 75(1): pp. 61-85, (month unavailable) 1973.
Kuznik, et al., "Blood Coagulation in stimulation of the vagus nerve in cats," Biull. Eskp. Biol. Med., vol. 78(7): pp. 7-9, (month unavailable) 1974.
Kuznik, et al., "Heart as an efferent regulator of the process of blood coagulation and fibrinolysis," Kardiologiia, vol. 13(3): pp. 10-17, (month unavailable) 1973.
Kuznik, et al., "Role of the heart and vessels in regulating blood coagulation and fibrinolysis," Kagdiologiia, vol. 13(4): pp. 145-154, (month unavailable) 1973.
Kuznik, et al., "Secretion of blood coagulation factors into saliva under conditions of hypo-and hypercoagulation," Voprosy Meditsinskoi Khimii, vol. 19(1): pp. 54-57; (month unavailable) 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (month unavailable) 1975.
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; (month unavailable) 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor—alpha by human monocuclear cells, Immunopharmacology, vol. 35, No. 1, pp. 47-51, Oct. 1996.
Martindale: The Extra Pharmacopoeia; 28th Ed. London; The pharmaceutical press; pp. 446-485; (month unavailable) 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, (month unavailable) 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; (month unavailable) 2004.
Mishchenko, et al., "Coagulation of the blood and fibrinolysos in dogs during vagal stimulation," Sechenov Physiological Journal of the USSR, vol. 61(1): pp. 101-107, (month unavailable) 1975.
Mishchenko, "The role of specific adreno- and choline-receptors of the vascular wall in the regulation of blood coagulation in the stimulation of the vagus nerve," Biull. Eskp. Biol. Med., vol. 78(8): pp. 19-22, (month unavailable) 1974.
Molina et al., CNI-1493 attenuates hemodynamic and pro-inflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Palmblad et al., Dynamics of early synovial cytokine expression in rodent collagen-induced arthritis: a thereapeutic study unding a

(56) References Cited

OTHER PUBLICATIONS macrophage-deactivation compound, American Journal of Pathology, vol. 158, No. 2, pp. 491-500, Feb. 2, 2001.
Pateyuk, et al.,"Treatment of Botkin's disease with heparin," Klin. Med., vol. 51(3): pp. 113-117, Mar. 1973.
Payne, J. B. et al., Nicotine effects on PGE2 and IL-1 beta release by LPS-treated human monocytes, J. Perio. Res., vol. 31, No. 2, pp. 99-104, Feb. 1996.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-5, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Rinner et al.; Rat lymphocytes produce and secrete acetylcholine in dependence of differentiation and activation; J.Neuroimmunol.; 81(1-2); pp. 31-37; Jan. 1998.
Romanovsky, A. A., et al.,The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, (month unavailable) 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, (month unavailable) 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95, pp. 31-35, (month unavailable) 1998.
Sternberg, E. M., Perspectives series: cytokines and the brain 'neural-immune interactions in health and disease,' J. Clin. Invest., vol. 100, No. 22, pp. 2641-2647, Dec. 1997.
Strojnik et al.; Treatment of drop foot using and implantable peroneal underknee stimulator; Scand. J. Rehab. Med.; vol. 19(1); pp. 37R43; (month unavailable) 1987.
Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Sykes, et al., An investigation into the effect and mechanisms of action of nicotine in inflammatory bowel disease, Inflamm. Res., vol. 49, pp. 311-319, Jul. 2000.
Takeuchi et al., A comparision between chinese blended medicine "Shoseiryuto" tranilast and ketotifen on the anit-allergic action in the guinea pigs, Allergy, vol. 34, No. 6, pp. 387-393, Jun. 1985 (eng. abstract).
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J. et al., Shock and tissue injury induced by recombinant human cachectin, Science, vol. 234, pp. 470-474, Oct. 24, 1986.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Van Der Horst et al.; Stressing the role of FoxO proteins in lifespan and disease; Nat Rev Mol Cell Biol.; vol. 8; No. 6; pp. 440-50; Jun. 2007.
Vanhoutte, et al., Muscarinic and beta-adrenergic prejunctional modulation of adrenergic neurotransmission in the blood vessel wall, Gen Pharmac., vol. 14, pp. 35-37, (month unavailable) 1983.
vanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, (month unavailable) 2000.
Vijayaraghavan, S.; Glial-neuronal interactions-implications for plasticity anddrug addictionl AAPS J.; vol. 11; No. 1; pp. 123-132; Mar. 2009.

(56) References Cited

OTHER PUBLICATIONS

Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.

Von KäNAL, et al., Effects of non-specific ?-adrenergic stimulation and blockade on blood coagulation in hypertension, J. Appl. Physiol., vol. 94, pp. 1455-1459, Apr. 2003.

Von KäNAL, et al., Effects of sympathetic activation by adrenergic infusions on hemostasis in vivo, Eur. J. Haematol., vol. 65: pp. 357-369, Dec. 2000.

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jun. 9, 1999.

Waserman, S. et al., TNF-? dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-6; Feb. 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yeh, S.S. et al., Geriatric cachexia: the role of cytokines, Am. J. Clin. Nutr., vol. 70(2), pp. 183-197, Aug. 1999.

Zhang et al., Tumor necrosis factor, The Cytokine Handbook, 3rd ed., Ed. Thompson, Academic Press, pp. 517-548, Jul. 1, 1998.

Zhang et al.; Roles of SIRT1 in the acute and restorative phases following induction of inflammation.; J Biol Chem.; vol. 285; No. 53; pp. 41391-401; Dec. 2010.

Levine, Jacob A.; U.S. Appl. No. 13/338,185 entitled "Modulation of sirtuins by vagus nerve stimulation" filed Dec. 27, 2011.

Robinson et al.; Studies with the Electrocardiograph on the Action of the Vagus Nerve on the Human Heart; J Exp Med; 14(3):217-234; Sep. 1911.

Tracey, K. J.; Reflex control of immunity; Nat Rev Immunol; 9(6); pp. 418-428; Jun. 2009.

Faltys et al.; U.S. Appl. No. 14/082,047 entitled "Neural Stimulation Devices and Systems for Treatment of Chronic Inflammation," filed Nov. 15, 2013.

\* cited by examiner

1) CAP was activated by a single supra-threshold pulse
2) The suppressive effect on LPS-induced TNF at 3hr post-stimulation was equivalent from 1 to 3000 pulses Single-pulse NCAP effects suppression of LPS-inducible TNF at 3h and 24h post-stimulation

SINGLE-PULSE ACTIVATION OF THE CHOLINERGIC ANTI-INFLAMMATORY PATHWAY TO TREAT CHRONIC INFLAMMATION

CROSS REFERENCE TO RELATED APPLICATIONS

This application claims the benefit of U.S. Provisional Application No. 61/484,112, filed on May 9, 2011, which is hereby incorporated by reference in its entirety. This patent application may be related to any of the following patent and pending U.S. application Ser. No. 12/434,462, filed on May 1, 2009 and entitled "VAGUS NERVE STIMULATION ELECTRODES AND METHODS OF USE"; U.S. application Ser. No. 12/620,413, filed Nov. 17, 2009 and entitled "DEVICES AND METHODS FOR OPTIMIZING ELECTRODE PLACEMENT FOR ANTI-INFLAMMATORY STIMULATION"; U.S. application Ser. No. 12/874,171, filed Sep. 1, 2010 and entitled "PRESCRIPTION PAD FOR TREATMENT OF INFLAMMATORY DISORDERS"; U.S. application Ser. No. 12/917,197, filed Nov. 1, 2010 and entitled "MODULATION OF THE CHOLINERGIC ANTI-INFLAMMATORY PATHWAY TO TREATMENT OR ADDICTION"; U.S. application Ser. No. 12/978,250, filed Dec. 23, 2010 and entitled "NEURAL STIMULATION DEVICES AND SYSTEMS FOR TREATMENT OF CHRONIC INFLAMMATION"; and U.S. application Ser. No. 12/797,452, filed Jun. 9, 2010 and entitled "NERVE CUFF WITH POCKET FOR LEADLESS STIMULATOR."

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The present invention relates generally to systems and devices for treatment of disorders, including chronic inflammation and inflammatory disorders using extremely low duty-cycle stimulation. In particular, described herein are systems, devices and methods for treating disorders such as intestinal inflammatory disorders. Further described herein generally are methods and devices, including an implantable microstimulators, adapted for electrically stimulating the vagus nerve to treat chronic inflammation by extremely low duty cycle stimulation to modulate an inflammatory response (via the nicotinic cholinergic anti-inflammatory pathway).

BACKGROUND OF THE INVENTION

Electrical stimulation of the neural cholinergic anti-inflammatory pathway (CAP or NCAP) has been described in the literature, beginning with the seminal work of Kevin Tracey (see, e.g., Tracey, K J "Physiology and immunology of the cholinergic antiinflammatory pathway." *The Journal of clinical investigation* 2007:117 (2): 289-96), who first identified the cholinergic anti-inflammatory pathway and characterized the link between vagus nerve stimulation and inhibition of inflammation by suppressing cytokine production. Since then, research as continued to explore the relationship between stimulation of the CAP and modulation of inflammatory disorders. Typical stimulation parameters have include stimulation by a burst of pulses (e.g., between 10 Hz to 1 GHz for between 30 sec and 20 min), with a slight increase in effect seen at higher frequencies (see, e.g., US 2009/0143831 to Huston et al.).

Although this work has suggested that chronic inflammation may be successfully treated by an implantable stimulator, the design and implementation of such a chronically implantable and usable stimulator has proven elusive, in part because of the power demands that a device capable of truly long-term, chronic, usage would face.

Implantable electrical stimulation devices have been developed for therapeutic treatment of a wide variety of diseases and disorders. For example, implantable cardioverter defibrillators (ICDs) have been used in the treatment of various cardiac conditions. Spinal cord stimulators (SCS), or dorsal column stimulators (DCS), have been used in the treatment of chronic pain disorders including failed back syndrome, complex regional pain syndrome, and peripheral neuropathy. Peripheral nerve stimulation (PNS) systems have been used in the treatment of chronic pain syndromes and other diseases and disorders. Functional electrical stimulation (FES) systems have been used to restore some functionality to otherwise paralyzed extremities in spinal cord injury patients.

Recently, implantable vagus nerve stimulations have been developed, including vagus nerve stimulators to treat inflammation. Such implants typically require an electrode and a power source. The size and use-limiting parameters may typically be the power requirements, which either require a long-lasting (and therefore typically large) battery, or require the added complication of charging circuitry and charging devices.

For example, typical implantable electrical stimulation systems may include one or more programmable electrodes on a lead that are connected to an implantable pulse generator (IPG) that contains a power source and stimulation circuitry. Even relatively small implantable neural stimulator technology, i.e. microstimulators, having integral electrodes attached to the body of a stimulator may share some of these disadvantages, as the currently developed leadless devices tend to be larger and more massive than desirable, making it difficult to stably position such devices in the proper position with respect to the nerve.

We herein describe the surprising result that long-lasting, robust inhibition of inflammation may be achieved by on a single (or very few) supra-threshold electrical pulse applied to the vague nerve. This finding is particularly surprising given the extraordinarily robust effect despite the minimal power applied, particularly compared to published data showing effects at much higher applied energy. These findings support various extremely low-power devices, system and methods for treating chronic inflammation. In particular, devices and methods for the treatment of inflammatory disorders, including inflammatory disorders of the intestine (e.g., irritable bowel disorder or IBD) are described, including microstimulators and methods of using them based on the remarkably low power requirements identified.

SUMMARY

Described herein are devices, systems and methods for the extraordinarily low duty cycle stimulation of the vagus nerve. An extraordinarily low, extremely low, super low, or ultra low duty cycle refers generally to a duty cycle that provides stimulation using both a low number of electrical pulses per time period and a low stimulation intensity such that power requirements of the duty cycle are very low. The following are examples of various embodiments of extraordinarily low, extremely low, super low, or ultra low duty cycles. In some embodiments, the number of electrical pulses can be between 1 and 5, in one pulse increments, every 4 to 48 hours, in 4 hour increments. In some embodiments, the stimulation intensity can be at a supra-threshold level that is capable of effecting the desired physiological response through the vagus nerves. In some embodiments, the supra-threshold level is between about 100 µA and 5000 µA, or between about 100 µA and 4000 µA, or between about 100 µA and 3000 µA, or between about 100 µA and 2000 µA. In some embodiments, the supra-threshold level is less than about 2000 µA, 3000 µA, 4000 µA or 5000 µA.

In some embodiments, the duty cycle is one supra-threshold pulse every 4 hours, with the pulse amplitude less than about 2000 µA. In some embodiments, the duty cycle is one pulse every 4 hours, with the pulse amplitude less than about 3000 µA. In some embodiments, the duty cycle is one pulse every 12 hours, with the pulse amplitude less than about 2000 µA. In some embodiments, the duty cycle is one pulse every 12 hours, with the pulse amplitude less than about 3000 µA. In some embodiments, the duty cycle is one pulse every 24 hours, with the pulse amplitude less than about 2000 µA. In some embodiments, the duty cycle is one pulse every 24 hours, with the pulse amplitude less than about 3000 µA. In some embodiments, the duty cycle is one pulse every 48 hours, with the pulse amplitude less than about 2000 µA. In some embodiments, the duty cycle is one pulse every 48 hours, with the pulse amplitude less than about 3000 µA.

In some embodiments the pulse width can be between about 100 to 1000 µS, or can be about or less than about 100, 200, 300, 400, 500, 600, 700, 800, 900 or 1000 µS. In some embodiments, the frequency can be about or less than about 10, 20, 30, 40, 50, 60, 70, 80, 90 or 100 Hz. In some embodiments, the IPI can be about or less than about 100, 200, 300, 400, 500, 600, 700, 800, 900 or 1000 µS.

In some embodiments, a system for treating chronic inflammation and/or an inflammatory disorder in a patient is provided. The system includes an implantable microstimulator configured to apply a low duty-cycle stimulation to a vagus nerve, wherein the low duty-cycle stimulation provides no more than a single supra-threshold pulse every four hours; and a controller configured to set a dose for the microstimulator wherein the dose comprises the single supra-threshold pulse followed by an off-period of at least four hours. In some embodiments, the off-period is at least 24 hours, or at least 48 hours, or between about 4 to 48 hours, or between about 12 to 48 hours, or between about 24 to 48 hours. In some embodiments, the single supra-threshold pulse has a pulse amplitude of less than 5 mA, less than 3 mA, or less than 2 mA. In some embodiments, the single supra-threshold pulse is biphasic. In some embodiments, the chronic inflammation is intestinal inflammation. In some embodiments, the chronic inflammation is inflammatory bowel disease. In some embodiments, the chronic inflammation is Crohn's disease.

In some embodiments, a method of treating chronic inflammation and/or inflammatory disorders in a patient is provided. The method includes implanting a microstimulator; and applying only a single supra-threshold stimulus pulse from the microstimulator to the vagus nerve followed by an off-time of at least 4 hours. In some embodiments, the off-time is at least 24 hours, at least 48 hours, or between about 4 to 48 hours, or between about 12 to 48 hours, or between about 24 to 48 hours. In some embodiments, the single supra-threshold stimulus pulse has a pulse amplitude of less than 5 mA, less than 3 mA, or less than 2 mA. In some embodiments, the single supra-threshold stimulus pulse is biphasic. In some embodiments, the chronic inflammation is intestinal inflammation. In some embodiments, the chronic inflammation is inflammatory bowel disease. In some embodiments, the chronic inflammation is Crohn's disease.

Types of inflammatory disorders that may be treated as described herein include a variety of disease states, including diseases such as hay fever, atherosclerosis, arthritis (rheumatoid, bursitis, gouty arthritis, polymyalgia rheumatic, etc.), asthma, autoimmune diseases, chronic inflammation, chronic prostatitis, glomerulonephritis, nephritis, inflammatory bowel diseases, pelvic inflammatory disease, reperfusion injury, transplant rejection, vasculitis, myocarditis, colitis, etc.

Non-limiting examples of inflammatory disorders which can be treated using the present invention include appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitits, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitits, pneumoultramicroscopic silicovolcanoconiosis, alvealitis, bronchiolitis, pharyngitis, pleurisy, sinusitis, influenza, respiratory syncytial virus infection, HIV infection, hepatitis B virus infection, hepatitis C virus infection, herpes virus infection disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, Type II diabetes, ankylosing spondylitis, Berger's disease, Reiter's syndrome, Hodgkin's disease, ileus, hypertension, irritable bowel syndrome, myocardial infarction, sleeplessness, anxiety and stent thrombosis.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
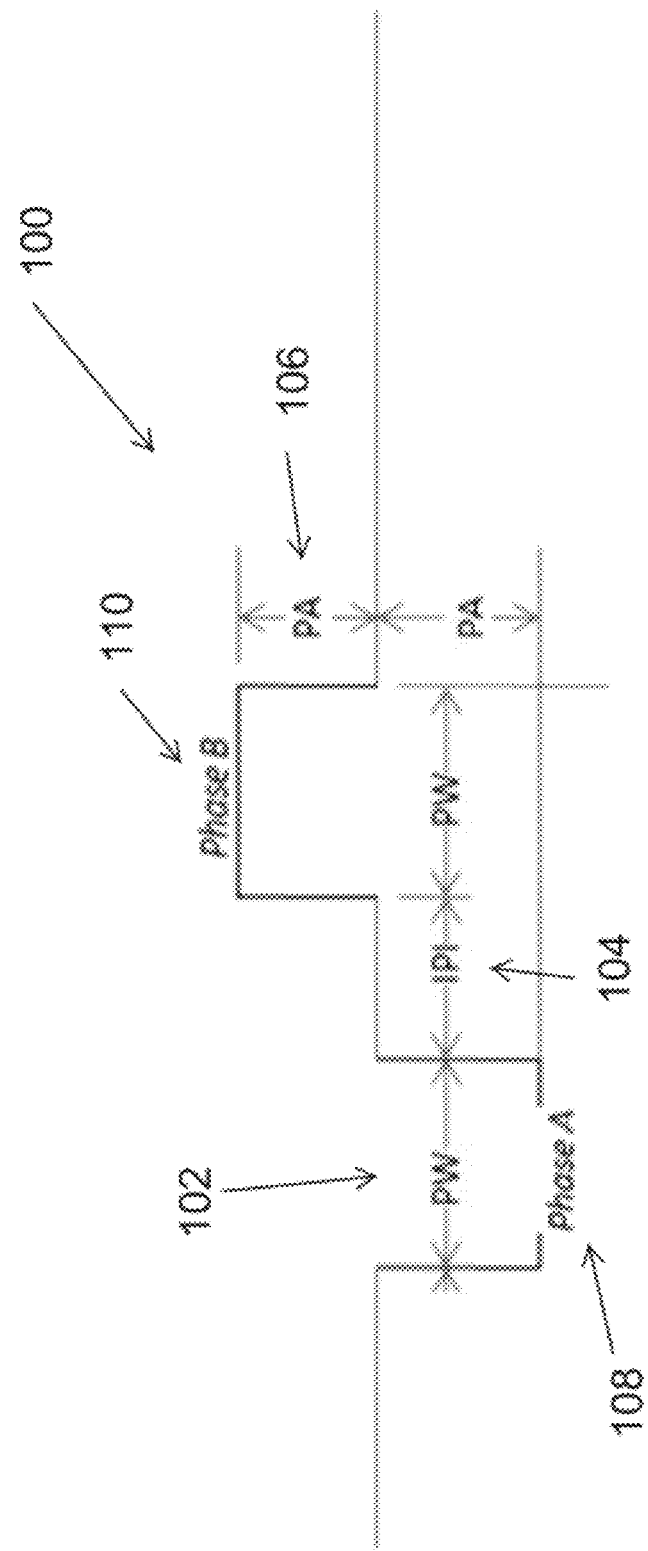
FIG. 1 is a diagram of a single stimulation waveform.

In general, described herein are systems, methods and devices illustrating extraordinarily low duty cycle stimulation of the vagus nerve to treat a disorder. In particular, described herein are systems, methods and devices illustrating extraordinarily low duty cycle stimulation of the vagus nerve to reduce or prevent inflammation and the effects of inflammation in a mammalian model. An extraordinarily low, extremely low, super low, or ultra low duty cycle refers generally to a duty cycle that provides stimulation using both a low number of electrical pulses per time period and a low stimulation intensity such that power requirements of the duty cycle are very low. The methods described herein apply various stimulation protocols that may be used to significantly reduce inflammation and/or the effects of inflammation. Simulation parameters that may be varied include the pulse shape (e.g., sinusoidal, square, biphasic, monophasic, etc.) the duration of stimulation, the on-time, the off-time, the inter-pulse interval, or the like. One key factor examined herein is the number of supra-threshold pulses. As shown herein, the stimulation of the vagus nerve with even a single supra-threshold stimulus results in a significant and long-lasting effect, even when compared to multiple stimulations. This effect was particularly profound when examined using a rodent model for IBD.

The following are examples of various embodiments of extraordinarily low, extremely low, super low, or ultra low duty cycles. In some embodiments, the number of electrical pulses can be between 1 and 5, in one pulse increments, every 4 to 48 hours, in 4 hour increments. In some embodiments, the stimulation intensity can be at a supra-threshold level that is capable of effecting the desired physiological response through the vagus nerves. In some embodiments, the supra-threshold level is between about 100 µA and 5000 µA, or between about 100 µA and 4000 µA, or between about 100 µA and 3000 µA, or between about 100 µA and 2000 µA. In some embodiments, the supra-threshold level is less than about 2000 µA, 3000 µA, 4000 µA or 5000 µA.

In some embodiments, the duty cycle is one supra-threshold pulse every 4 hours, with the pulse amplitude less than about 2000 µA. In some embodiments, the duty cycle is one pulse every 4 hours, with the pulse amplitude less than about 3000 µA. In some embodiments, the duty cycle is one pulse every 12 hours, with the pulse amplitude less than about 2000 µA. In some embodiments, the duty cycle is one pulse every 12 hours, with the pulse amplitude less than about 3000 µA. In some embodiments, the duty cycle is one pulse every 24 hours, with the pulse amplitude less than about 2000 µA. In some embodiments, the duty cycle is one pulse every 24 hours, with the pulse amplitude less than about 3000 µA. In some embodiments, the duty cycle is one pulse every 48 hours, with the pulse amplitude less than about 2000 µA. In some embodiments, the duty cycle is one pulse every 48 hours, with the pulse amplitude less than about 3000 µA.

The examples described herein use a stimulator and stimulation control package that was developed for use in driving vagus nerve stimulation. In some example, the stimulation is controlled by a software package that is configured to run on a microprocessor (e.g., personal computer) and to control output of an emulator/stimulator (which may be referred to as an "ITE" or integrated terminal emulator). Thus, the systems described herein may include logic (e.g., control logic) that may be software, firmware, and/or hardware to control the application of stimulation. For example, in some variations, the parameters controlling stimulation and data acquisition may include: (1) selected stimulating electrode pair including a cathode and anode; (2) frequency in 1 Hz increments; (3) Pulse Width (PW): 20-2,000 uS in 1 uS increments; (4) Pulse Amplitude (PA): ±0-5,000 uA in 3 uA increments; and (5) Inter-Pulse-Interval between phase A & B of waveform (IPI): 20-2,000 uS in 1 uS increments.

In addition to the exemplary parameters provided above, in some embodiments the PW can be between about 100 to 1000 µS, or can be about or less than about 100, 200, 300, 400, 500, 600, 700, 800, 900 or 1000 µS. In some embodiments, the frequency can be about or less than about 10, 20, 30, 40, 50, 60, 70, 80, 90 or 100 Hz. In some embodiments, the IPI can be about or less than about 100, 200, 300, 400, 500, 600, 700, 800, 900 or 1000 µS.

For example, the exemplary waveform shown on FIG. 1 is a biphasic (charge balanced) waveform 100 that includes two symmetric pulse widths 102 (PW) separated by an inter-pulse interval 104 (IPI). The pulse widths 102 have a pulse amplitude 106 (PA) that is also symmetric for the first phase 108 (phase A) and the second phase 110 (phase B) of the biphasic stimulus, with a negative pulse amplitude in phase A and a positive amplitude in phase B. Other pulse waveforms may be used. In some embodiments, the pulse waveforms may be non-biphasic and/or may have asymmetric pulse widths and/or asymmetric pulse amplitudes.

The stimulator may generate a pulse train on a pair of electrodes. The pulses may be generated using a bipolar current source and can be capacitively isolated with >1 uF ceramic capacitors on both electrodes outputs. Compliance voltage can be set to as high as +/−18.8 volts.

The different experimental examples described herein show that appropriate NCAP stimulation of the vagus nerve can be used to limit or eliminate the effects of intestinal inflammation, in particular in a rat model of colitis and a rat model of Crohn's disorder. Based on this data, a biphasic simulation at the parameters described above may successfully treat intestinal inflammation.

Figure 2:
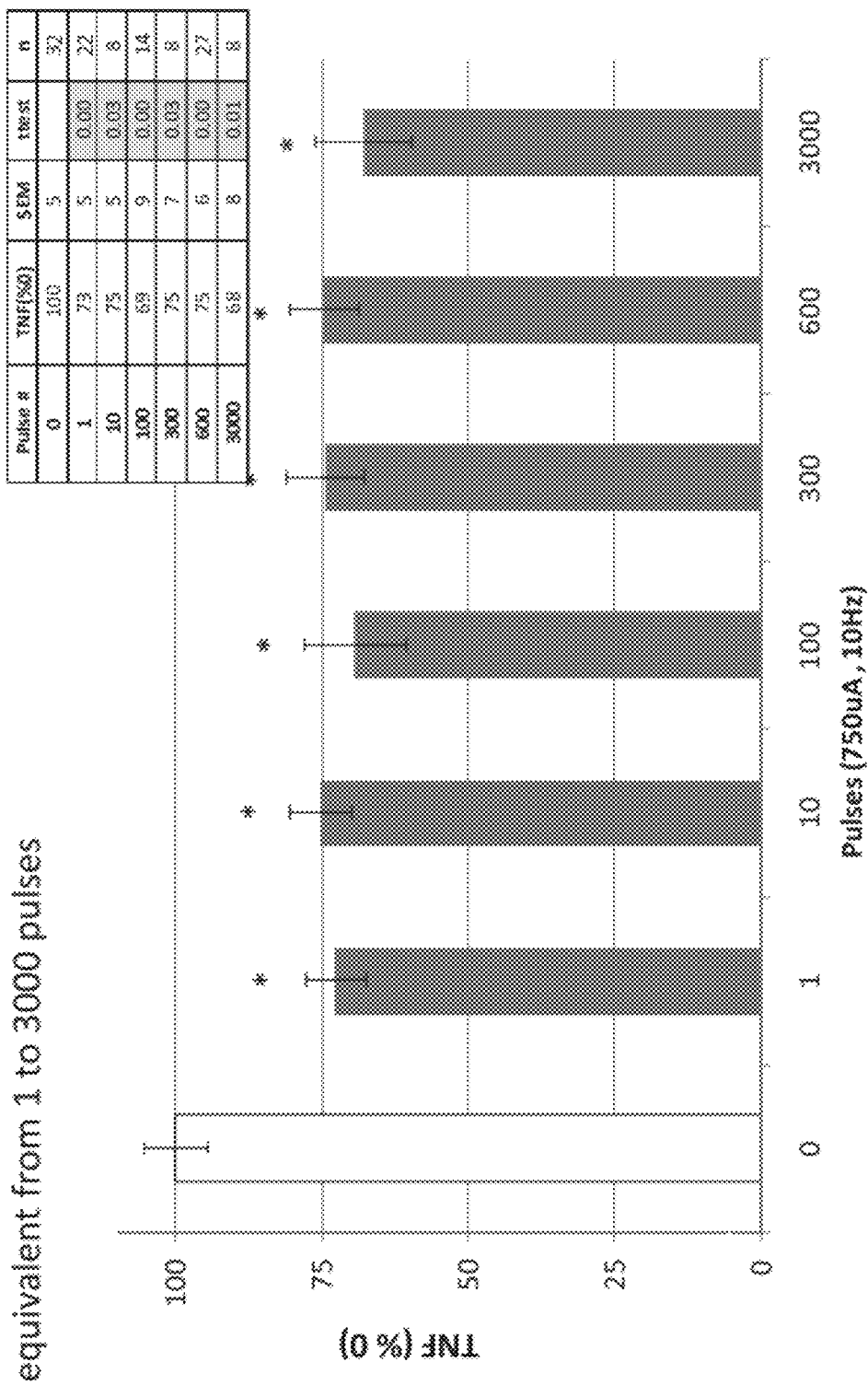
FIG. 2 is a graph comparing the effect on TNF levels from a single stimulation pulse with the effect from up to 3000 pulses.

In one example, mice (Male, BALB/c) were anesthetized and cuff electrodes (0.3 mm ID, 0.5 mm inter-electrode distance; Microprobes, Gaithersburg, Md.) were placed around the left carotid sheath (containing the cervical vagus nerve) and secured by suture. Supra-threshold pulses (750 µA, 200 µS, 10 Hz) were applied in various numbers (0, 1, 10, 100, 300, 600, 3000). Afterwards, the electrode was removed and the wound stapled closed. Mice recovered for 3 hours, and then were challenged with LPS (5 mg/kg; IP); these mice were sacrificed 90 minutes post-LPS and serum TNF measured by ELISA to measure the effects on inflammatory cytokines. As shown on FIG. 2, even a single supra-threshold stimulus resulted in a significant suppression of TNF at 3 hours after treatment. Thus, the effect was long lasting and the effect from a single pulse at 3 hours was equivalent to the effect generated by up to 3000 pulses.

Figure 3:
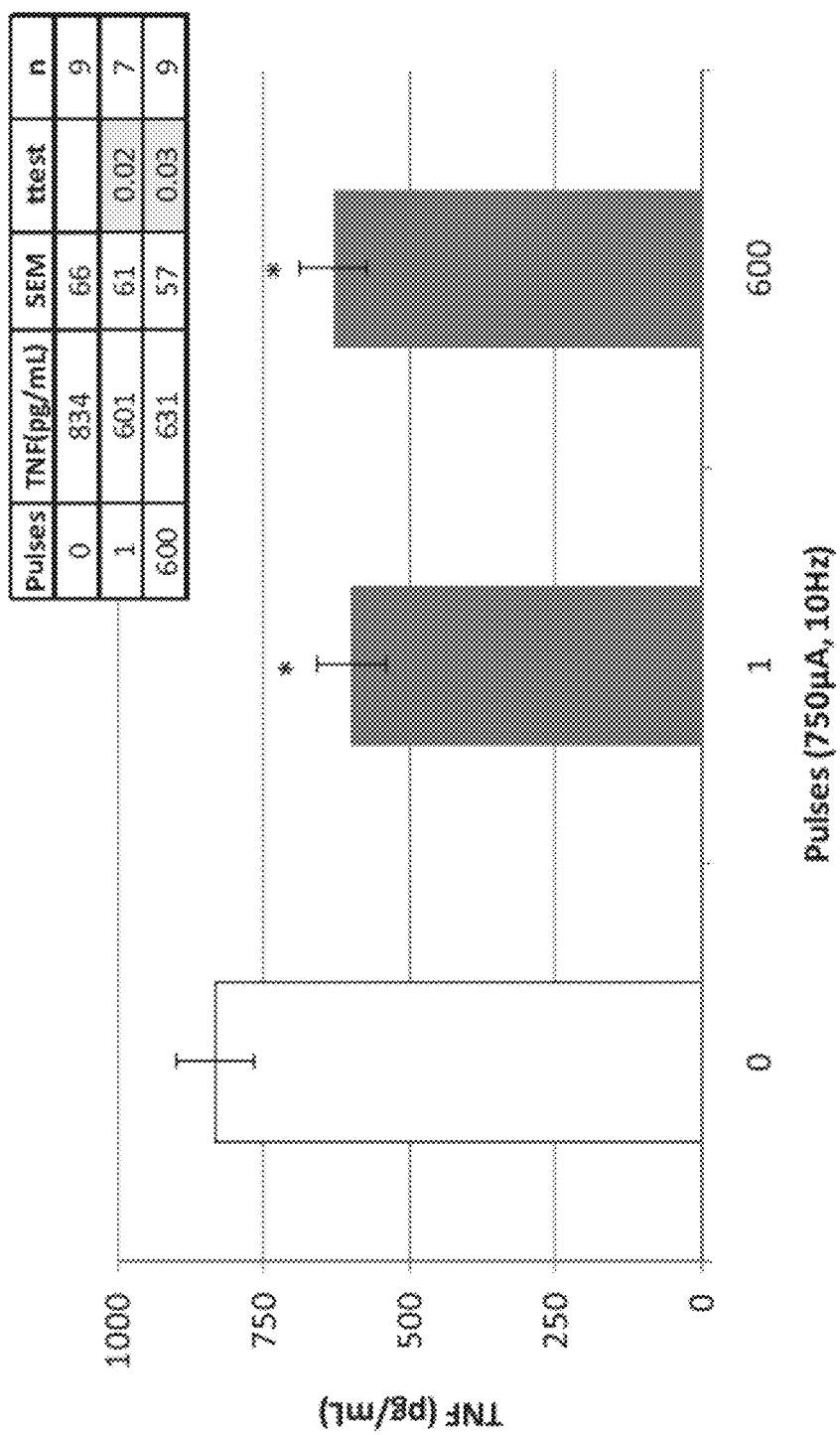
FIG. 3 is a graph illustrating the effect on TNF levels from a single stimulation pulse 24 hours post-stimulation.

A second similar experiment was conducted to examine the long lasting effect of a single supra-threshold pulse on the cholinergic anti-inflammatory pathway (CAP). Mice (Male, BALB/c) were anesthetized and cuff electrodes (0.3 mm ID, 0.5 mm inter-electrode distance; Microprobes, Gaithersburg, Md.) were placed around the left carotid sheath (containing the cervical vagus nerve) and secured by suture. Supra-threshold pulses (750 gA, 2000, 10 Hz) were applied in various numbers (0, 1, 600). Afterwards, the electrode was removed and the wound stapled closed. Mice recovered for 24 hours, and then were challenged with LPS (5 mg/kg; IP); these mice were sacrificed 90 minutes post-LPS and serum TNF measured by ELISA to measure the effects on inflammatory cytokines. As shown on FIG. 3, a single supra-threshold stimulus resulted in a significant suppression of TNF at 24 hours after treatment that was equivalent to the effect generated by 600 pulses.

Figure 4:
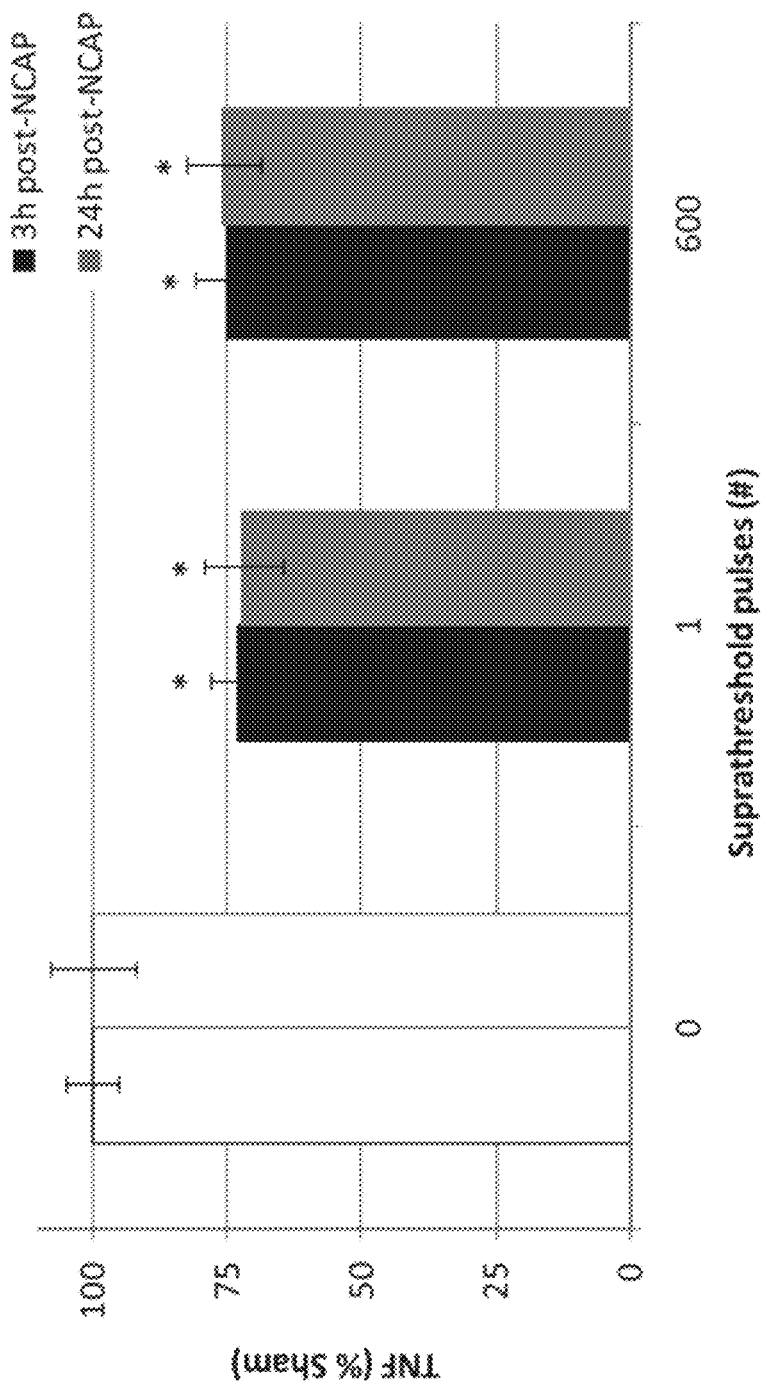
FIG. 4 is a graph illustrating the effect on TNF levels from a single stimulation pulse 3 hours and 24 hours post-stimulation.

FIG. 4 combines selected portions of the results of the two experiments described above to show that single pulse stimulation of the NCAP effects suppression of LPS-inducible TNF at 3 hours and 24 hours post-stimulation at the same effectiveness as 600 pulses.

Figure 5:
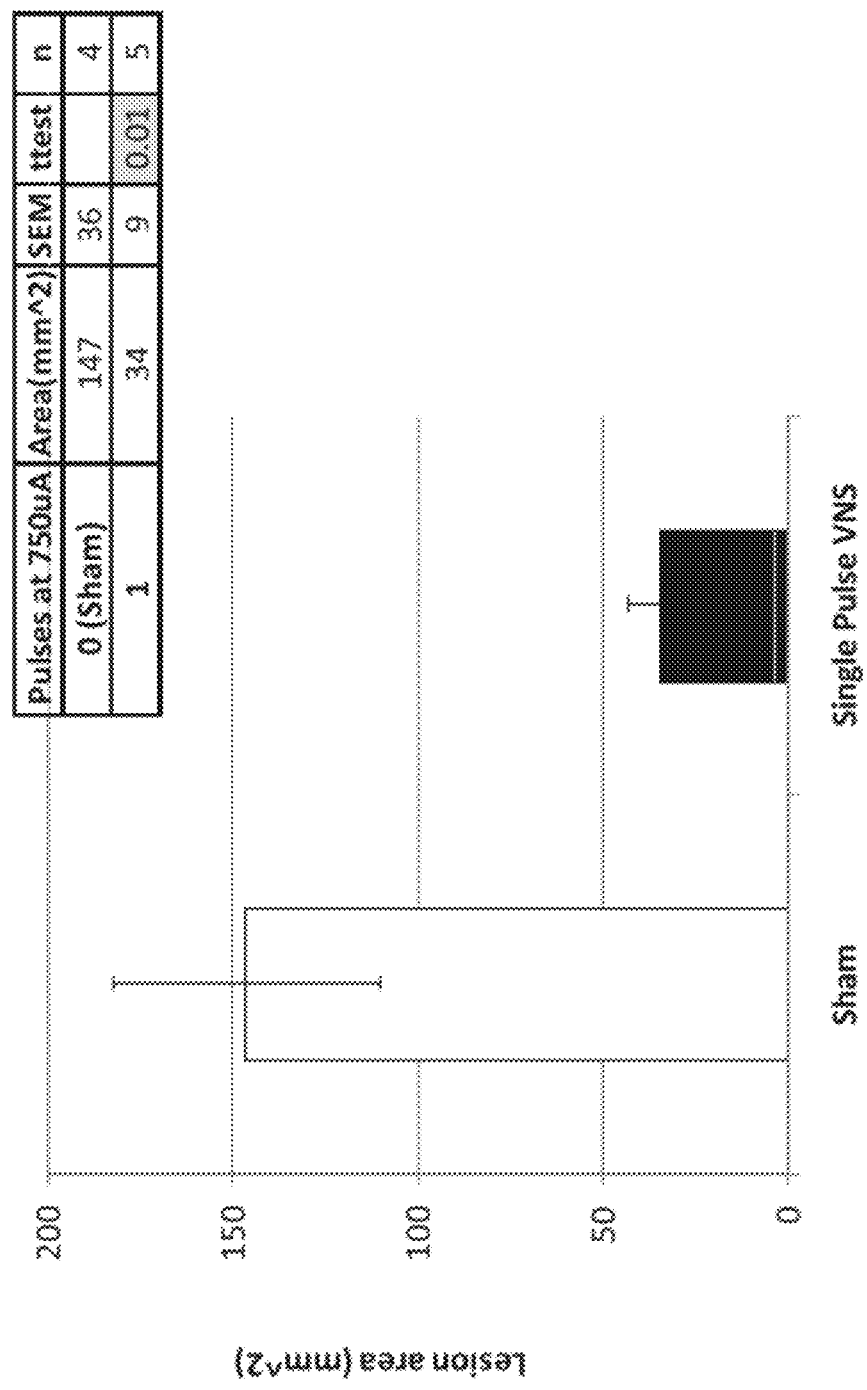
FIG. 5 is a graph illustrating the effect on lesion area in a rat model of IBD from a single stimulation pulse.

In another example, an experiment was conducted to determine the effectiveness of single pulse suppression of lesion area in a rat model for IBD/Crohn's disease. Rats were anesthetized and were either given a sham stimulation or a single supra-threshold stimulus to the left cervical vagus nerve (1 pulse at 750 µA, 2000 pulse width, 10 Hz). IBD was induced at 30 minutes post-stimulation by the SC injection of indomethacin (10 mg/kg (5 mg/mL) in 5% sodium bicarbonate). Lesions were stained in-life 23.5 hours post-indomethacin injection by anesthetizing the rats with isoflurane and IV tail injection with Evans Blue (0.3 ml of 1%). Rats were sacrificed via C02 asphyxiation at 24 hours post disease induction, and the small intestines were harvested, cleaned and fixed in 2% formalin overnight. Photographs were taken and digitized of the fixed intestines and lesions were quantified by a blinded scorer. As illustrated in FIG. 5, a single supra-threshold stimulus (750 µA, 200 µS pulse width, 10 Hz) resulted in a profound reduction in lesions.

Figure 6:
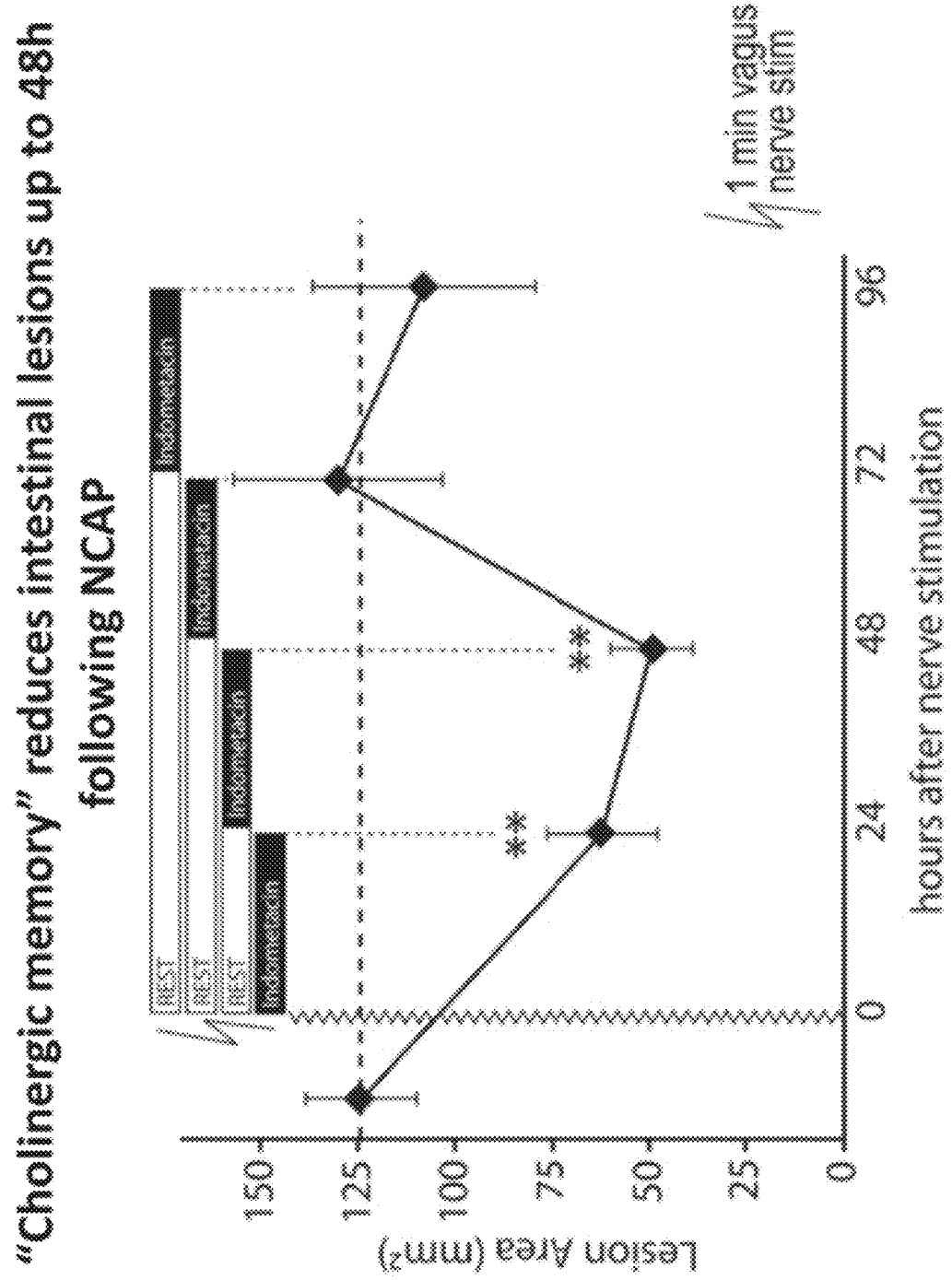
FIG. 6 is a graph illustrating the long term effect on lesion area in a rat model of IBD from a single stimulation pulse.

These results are even more significant, given the data shown in FIG. 6, which illustrates a "memory effect" of vagus nerve stimulation in a rat model of Crohn's disease. Rats were anesthetized and were either given a sham stimulation or an actual stimulation to the left cervical vagus nerve (1 mA, 200 µS pulse width, 10 Hz, 60 s). IBD/Crohn's disease was induced at various times (see FIG. 6) post-stimulation by the SC injection of indomethacin (10 mg/kg (5 mg/mL) in 5% sodium bicarbonate). Lesions were stained in-life 23.5 hours post-disease induction by anesthetizing the rats with isoflurane and IV tail injection with Evans Blue (0.3 ml of 1%). Rats were sacrificed via C02 asphyxiation at 24 hours post disease induction, and the small intestines were harvested, cleaned and fixed in 2% formalin overnight. Photographs were taken and digitized of the fixed intestines and lesions were quantified by a blinded scorer. In this example, a brief period of stimulation of the vagus nerve may result in a surprisingly long-lasting effect (e.g., up to 48 hours) in the reduction of intestinal lesions otherwise induced by the application of indomethacin. This data strongly suggests that stimulation may be provided extremely infrequently, with long (e.g., >48 hours) of "silent" periods without stimulation applied. Such extremely low duty-cycle stimulation for treating IBD may be particularly helpful in implantable systems, allowing extremely long battery life while having unexpectedly robust therapeutic benefits.

Although the examples provided above describe methods, systems and devices for treating an inflammatory disorder in a rat model, all the methods, systems and devices described herein can be used and/or adapted for use in other mammals, such as humans. For example, a system and method for treating an inflammatory disorder in a human using a single supra-threshold pulse and/or an extraordinarily low duty cycle stimulation protocol can include an electrode, such as a cuff electrode, that is configured to be implanted around the vagus nerve and deliver electrical stimulation to the vagus nerve of the patient. The system can further include a processor, memory for storing instructions, and/or a controller can include programming to deliver the low duty cycle stimulation protocol, including the single supra-threshold pulse protocol, to the vagus nerve via the cuff electrode. A battery can be provided to provide power for the system, and because the low duty cycle stimulation protocol consumes so little energy, the battery life can be greatly extended, allowing the system to be completely implanted within the patient for a long duration before the battery needs to be replaced or recharged. For an implanted system, this provides a great benefit since it can reduce the frequency of surgical procedures that may be required to change the battery.

The stimulation parameters used in this system can be the same or similar to the parameters disclosed above. For example, the pulse amplitude can be less than about 5, 4, 3, or 2 mA. In addition, the low duty cycle stimulation protocol can deliver a single supra-threshold pulse between off-times of between about 4 to 48 hours, or at least 4, 12, 24, or 48 hours. In some embodiments the pulse width can be between about 100 to 1000 µS, or can be about or less than about 100, 200, 300, 400, 500, 600, 700, 800, 900 or 1000 µS. In some embodiments, the frequency can be about or less than about 10, 20, 30, 40, 50, 60, 70, 80, 90 or 100 Hz. In some embodiments, the IPI can be about or less than about 100, 200, 300, 400, 500, 600, 700, 800, 900 or 1000 µS.

In general, these results suggest that the application of even a single brief supra-threshold stimulus of the vagus nerve may result in a substantial reduction in the effects of inflammation, possibly by inhibition of inflammatory cytokines such as TNF. These results are both surprising, given the prior arts tendency to stimulate for much longer times, and important for the design of future devices and methods. In particular, stimulation of the vagus nerve (or other portions of the inflammatory reflex) may be configured to apply extremely low duty-cycle stimulation. As mentioned briefly, this would allow for much smaller, lighter and more efficient implantable stimulation systems.

Types of inflammatory disorders that may be treated as described herein include a variety of disease states, including diseases such as hay fever, atherosclerosis, arthritis (rheumatoid, bursitis, gouty arthritis, polymyalgia rheumatic, etc.), asthma, autoimmune diseases, chronic inflammation, chronic prostatitis, glomerulonephritis, nephritis, inflammatory bowel diseases, pelvic inflammatory disease, reperfusion injury, transplant rejection, vasculitis, myocarditis, colitis, etc.

Non-limiting examples of inflammatory disorders which can be treated using the present invention include appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitits, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitits, pneumoultramicroscopic silicovolcanoconiosis, alvealitis, bronchiolitis, pharyngitis, pleurisy, sinusitis, influenza, respiratory syncytial virus infection, HIV infection, hepatitis B virus infection, hepatitis C virus infection, herpes virus infection disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, Type II diabetes, ankylosing spondylitis, Berger's disease, Reiter's syndrome, Hodgkin's disease, ileus, hypertension, irritable bowel syndrome, myocardial infarction, sleeplessness, anxiety and stent thrombosis.

Any of these disorders (e.g., inflammatory disorders) may be treated by, for example, implanting a cuff electrode around the vagus nerve, and using an extraordinarily low duty cycle stimulation protocol as described herein to treat. A processor and memory for storing instructions and/or programming can be used to control the stimulation protocol. The stimulation parameters used in this system and method can be the same or similar to the parameters disclosed above. For example, the pulse amplitude of the single supra-threshold pulse can be less than about 5, 4, 3, or 2 mA. In addition, the low duty cycle stimulation protocol can deliver a single supra-threshold pulse between off-times of between about 4 to 48 hours, or at least 4, 12, 24, or 48 hours. Any of these methods may include a step of determining the efficacy of the treatment. For example, any of these methods may include the step of monitoring the patient before and/or during treatment. For example, in treating an inflammatory disorder, a biomarker for inflammation may be monitored, such as a cytokine or other marker. In some variations, monitoring the patient may include assessing the patient visually (e.g., for swelling, body temperature, etc.). In some variations the systems described herein may include a sensor and/or data processing subsystem for monitoring the patient and/or the effect of the treatment with the system.

Although the examples and description above focuses primarily on inflammatory disorders, in some embodiment, the systems, devices and methods described herein can be used to treat non-inflammatory diseases or disorders. For example, the systems, devices and methods described herein can be used to activate, regulate, and/or modulate the levels of sirtuins by extraordinarily low duty cycle stimulation of the vagus nerve. The modulation of sirtuins by vagus nerve stimulation is also discussed in U.S. application Ser. No. 13/338,185, filed Dec. 27, 2011 and entitled "MODULATION OF SIRTUINS BY VAGUS NERVE STIMULATION," which is hereby incorporated by reference in its entirety for all purposes. As above, a cuff electrode can be implanted around the vagus nerve and a processor and memory for storing instructions and/or programming can be used to control the stimulation protocol. The stimulation parameters used in this system and method can be the same or similar to the parameters disclosed above. For example, the pulse amplitude of the single supra-threshold pulse can be less than about 5, 4, 3, or 2 mA. In addition, the low duty cycle stimulation protocol can deliver a single supra-threshold pulse between off-times of between about 4 to 48 hours, or at least 4, 12, 24, or 48 hours. In some embodiments the pulse width can be between about 100 to 1000 µS, or can be about or less than about 100, 200, 300, 400, 500, 600, 700, 800, 900 or 1000 µS. In some embodiments, the frequency can be about or less than about 10, 20, 30, 40, 50, 60, 70, 80, 90 or 100 Hz. In some embodiments, the IPI can be about or less than about 100, 200, 300, 400, 500, 600, 700, 800, 900 or 1000 µS.

As mentioned above, in some embodiments, the system, device, and/or method includes monitoring the effects of the stimulation on the disease being treated. For example, inflammation indicators or disease indicators or other indicators can be monitored to evaluate the efficacy of the treatment protocol, allowing the stimulation protocol to be adjusted based on the evaluation. Any one of the parameters described herein can be modulated based on the evaluation. For example, the pulse amplitude and/or the off time can be increased or decreased to optimize the treatment efficacy. Examples of indicators that can be monitored include TNF levels, lesion size, degree or level of inflammation, cytokine levels, pain levels, sirtuin levels, and the like.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiments whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What may be claimed is:

1. A system for treating chronic inflammation in a patient, the system comprising:
    an implantable microstimulator configured to apply a low duty-cycle stimulation to a vagus nerve, wherein the low duty-cycle stimulation provides no more than a single supra-threshold pulse every four hours; and
    a controller configured to set a dose for the microstimulator wherein the dose comprises the single supra-threshold pulse followed by an off-period of at least four hours, wherein the single supra-threshold pulse is configured to reduce a level of inflammation in the patient.

2. The system of claim 1, wherein the off-period is at least 24 hours.

3. The system of claim 1, wherein the off-period is at least 48 hours.

4. The system of claim 1, wherein the single supra-threshold pulse has a pulse amplitude of less than 5 mA.

5. The system of claim 1, wherein the single supra-threshold pulse has a pulse amplitude of less than 3 mA.

6. The system of claim 1, wherein the single supra-threshold pulse has a pulse amplitude of less than 2 mA.

7. The system of claim 1, wherein the single supra-threshold pulse is biphasic.

8. The system of claim 1, wherein the chronic inflammation is intestinal inflammation.

9. The system of claim 1, wherein the chronic inflammation is inflammatory bowel disease.

10. The system of claim 1, wherein the chronic inflammation is Crohn's disease.

11. A method of treating chronic inflammation in a patient, the method comprising:
  implanting a microstimulator; and
  applying only a single supra-threshold stimulus pulse from the microstimulator to the vagus nerve followed by an off-time of at least 4 hours; and
  reducing a level of inflammation in the patient.

12. The method of claim 11, wherein the off-time is at least 24 hours.

13. The method of claim 11, wherein the off-time is at least 48 hours.

14. The method of claim 11, wherein the single supra-threshold stimulus pulse has a pulse amplitude of less than 5 mA.

15. The method of claim 11, wherein the single supra-threshold stimulus pulse has a pulse amplitude of less than 3 mA.

16. The method of claim 11, wherein the single supra-threshold stimulus pulse has a pulse amplitude of less than 2 mA.

17. The method of claim 11, wherein the single supra-threshold stimulus pulse is biphasic.

18. The method of claim 11, wherein the chronic inflammation is intestinal inflammation.

19. The method of claim 11, wherein the chronic inflammation is inflammatory bowel disease.

20. The method of claim 11, wherein the chronic inflammation is Crohn's disease.

* * * * *